(12) United States Patent
Kim et al.

(10) Patent No.: US 7,485,327 B2
(45) Date of Patent: Feb. 3, 2009

(54) **COMPOSITION COMPRISING *MELISSA* LEAF EXTRACT FOR ANTI-ANGIOGENIC AND MATRIX METALLOPROTEINASE INHIBITORY ACTIVITY**

(75) Inventors: Min-Young Kim, Taejon (KR); Byung-Young Park, Taejon (KR); Chang-Hee Moon, Taejon (KR); Eun-Kyu Park, Taejon (KR); Kyoung-Mi Kim, Jeonju (KR)

(73) Assignee: AngioLab, Inc., Daejeon (KR)

( * ) Notice: Subject to any disclaimer, the term of this patent is extended or adjusted under 35 U.S.C. 154(b) by 885 days.

(21) Appl. No.: 10/460,951

(22) Filed: Jun. 12, 2003

(65) Prior Publication Data
US 2004/0009244 A1 Jan. 15, 2004

Related U.S. Application Data

(63) Continuation-in-part of application No. PCT/KR01/02148, filed on Dec. 12, 2001.

(51) Int. Cl.
*A61K 36/00* (2006.01)

(52) U.S. Cl. ........................... 424/774; 424/725

(58) Field of Classification Search .................. None
See application file for complete search history.

(56) References Cited

U.S. PATENT DOCUMENTS

| 4,419,349 | A | * | 12/1983 | Kojima et al. | 424/745 |
| 6,060,061 | A | * | 5/2000 | Breton et al. | 424/745 |
| 6,099,845 | A | | 8/2000 | Na et al. | |
| 6,153,208 | A | * | 11/2000 | McAtee et al. | 424/402 |
| 6,261,566 | B1 | * | 7/2001 | Pillai et al. | 424/769 |
| 6,416,769 | B1 | * | 7/2002 | Vromen | 424/401 |
| 6,485,756 | B1 | * | 11/2002 | Aust et al. | 424/725 |
| 2001/0024664 | A1 | * | 9/2001 | Obukowicz et al. | 424/725 |

FOREIGN PATENT DOCUMENTS

| FR | 2622110 | * | 4/1989 |
| JP | 02256621 | * | 10/1990 |
| JP | 06199647 | * | 7/1994 |
| JP | 07196526 | * | 8/1995 |
| JP | 08301779 | * | 11/1996 |
| JP | 09241142 | * | 9/1997 |
| JP | 11049693 | A | 2/1999 |
| JP | 11147834 | * | 6/1999 |

OTHER PUBLICATIONS

An et al. Natural Product Sciences. 1997. vol. 3, No. 1, pp. 29-37.*
PDR for Herbal Medicines. 1998. Publ. Medical Economics Co., Montvale, NJ. pp. 967-968/.*
Chlabicz and Galasinski, "The components of Melissa officinalis L. that influence protein biosynthesis in-vitro", J Pharm Pharmacol. Nov. 1986; 38(11):791-4 (Abstract only).

* cited by examiner

*Primary Examiner*—Christopher R. Tate
(74) *Attorney, Agent, or Firm*—Joseph Hyosuk Kim; JHK Law

(57) ABSTRACT

The present invention relates to a composition comprising *Melissa* leaf extract that inhibits angiogenesis and matrix metalloproteinase activity. The *Melissa* leaf extract of the present invention inhibits angiogenesis and activity of matrix metalloproteinase, so that it can be applied to treat or prevent diseases related to angiogenesis and matrix metalloproteinase. The composition of the present invention comprising *Melissa* leaf extract may also comprise more than one component of the other anti-angiogenic, anti-cancer, anti-inflammatory and anti-aging components. This particular composition comprising *Melissa* leaf extract can be used for pharmaceutical, dietetic and/or cosmetic purposes.

4 Claims, 9 Drawing Sheets

[FIG. 1]
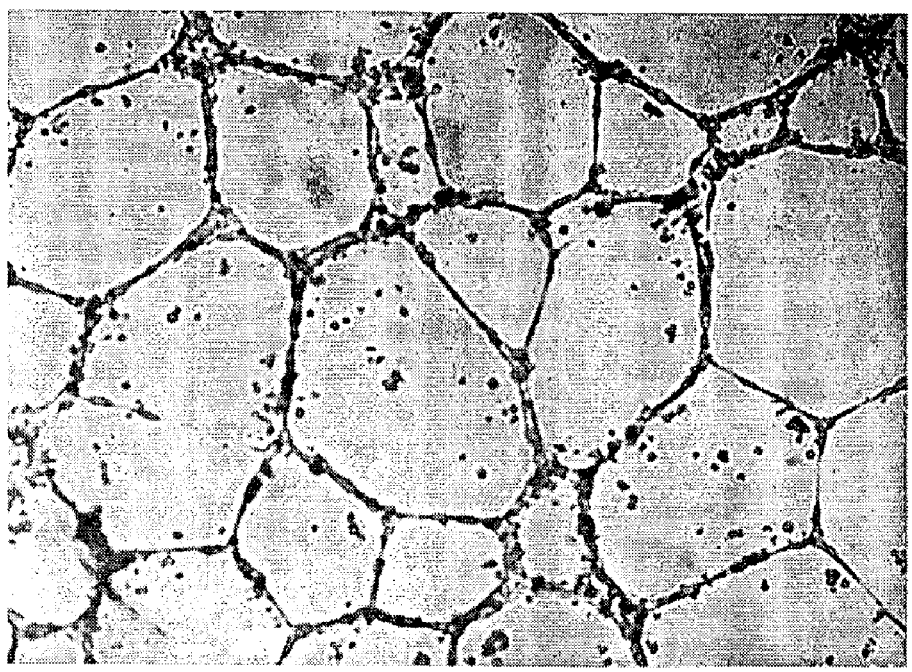
[FIG. 2]
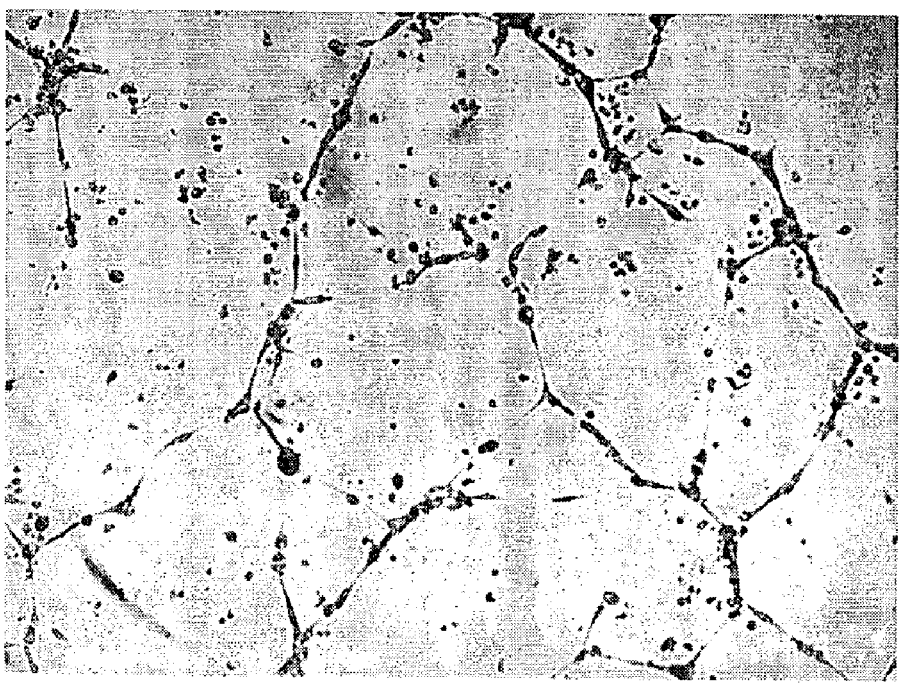

[FIG. 3]
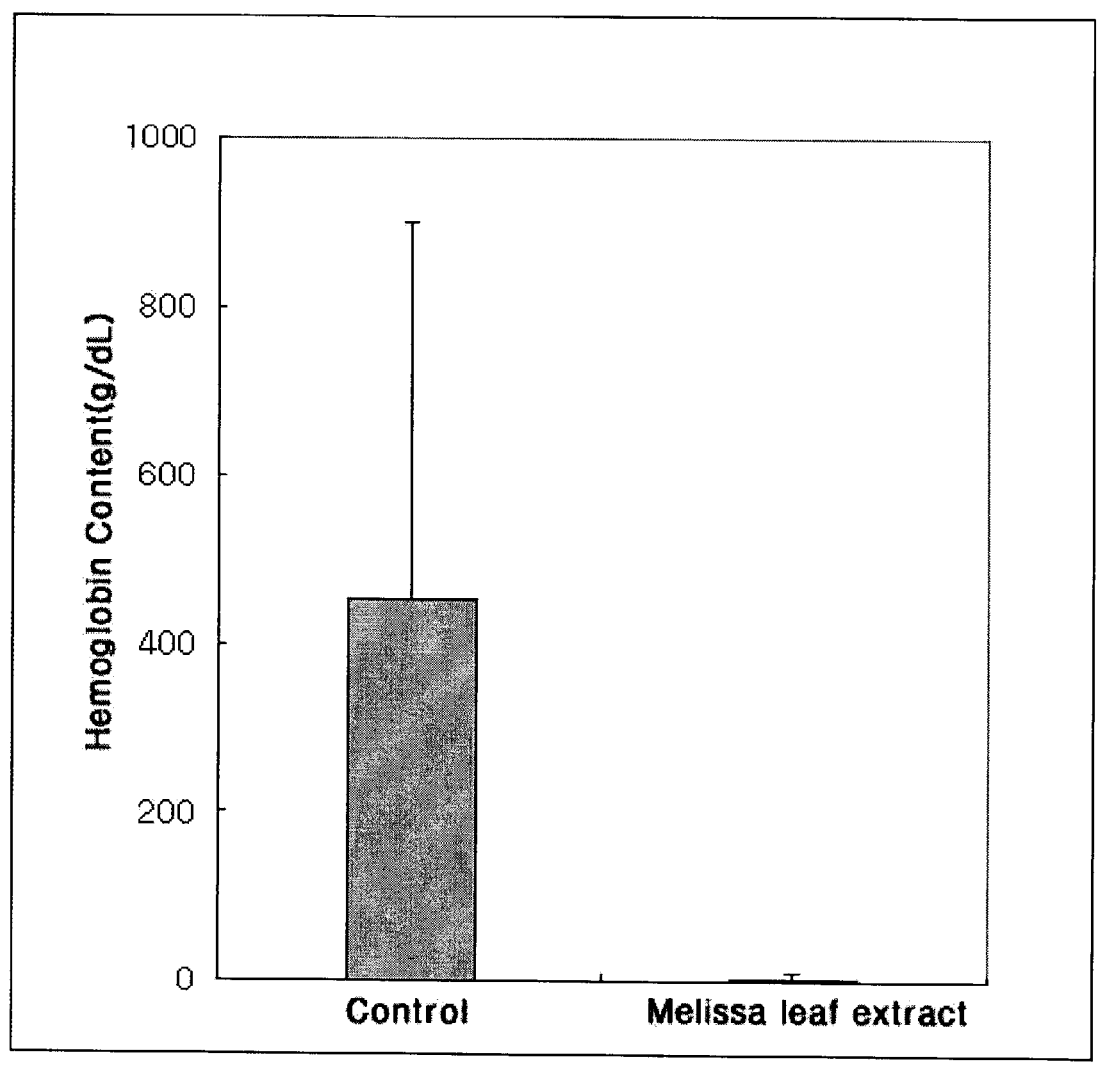

[FIG. 4]
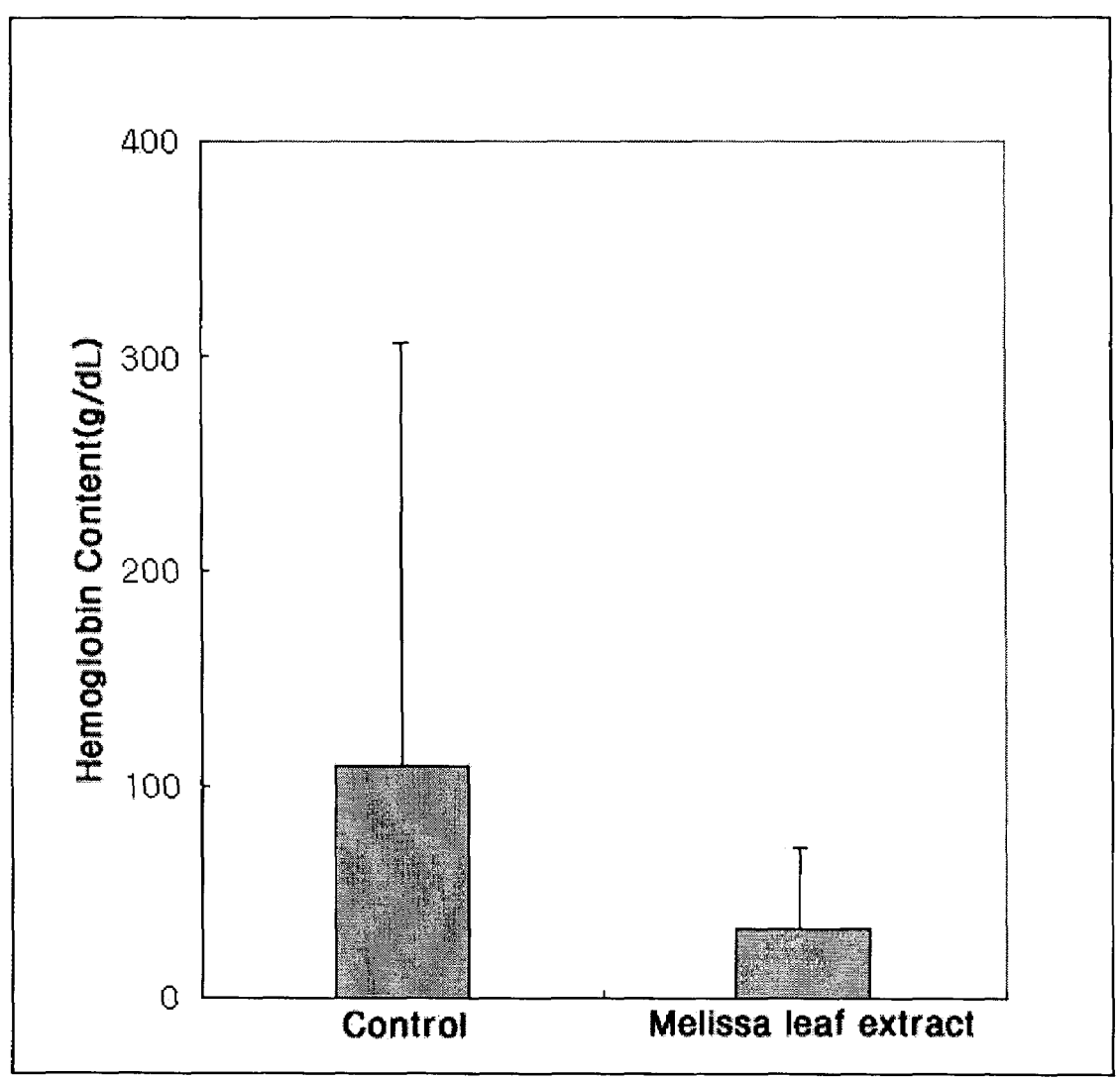

[FIG. 5]
A
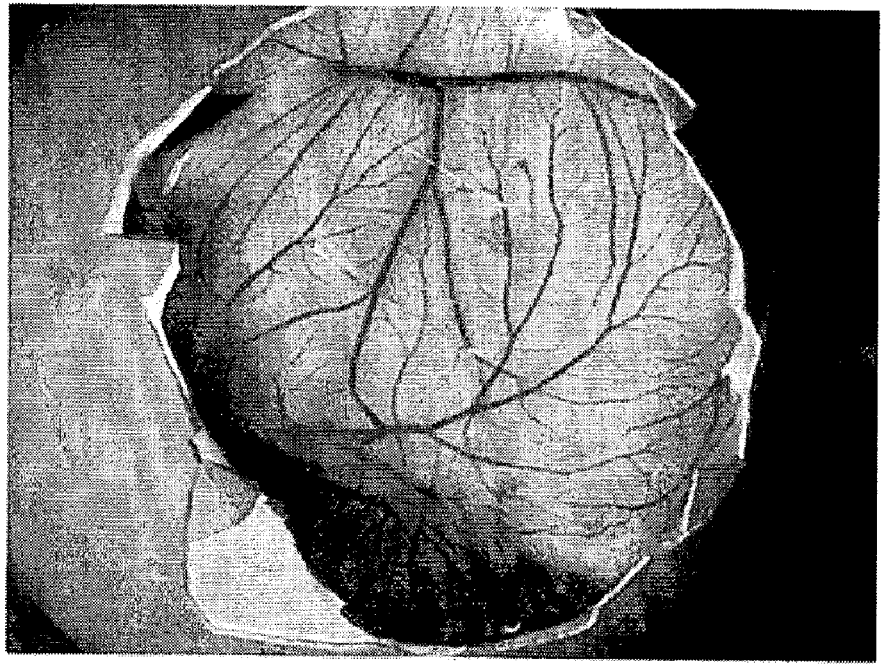
B
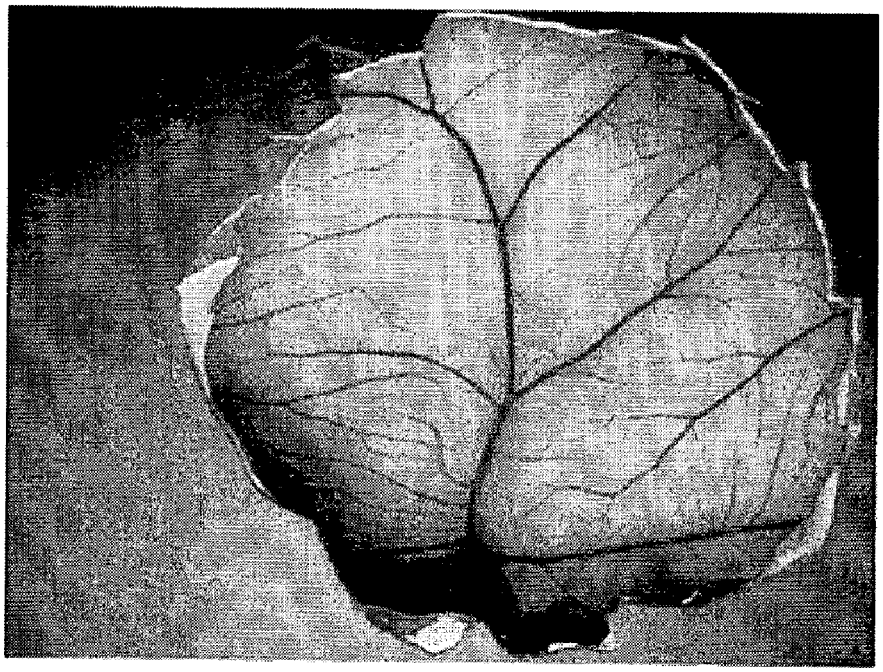

[FIG. 6]
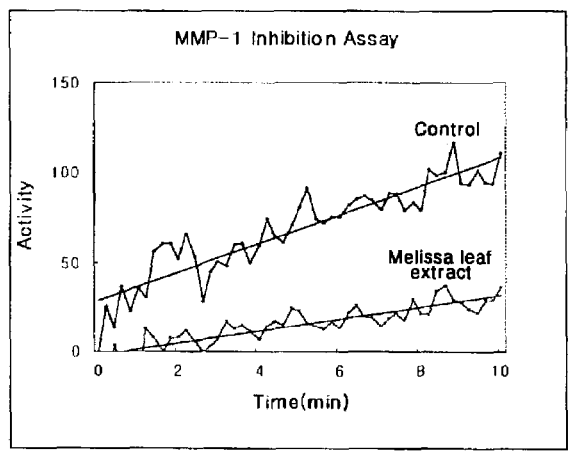
[FIG. 7]
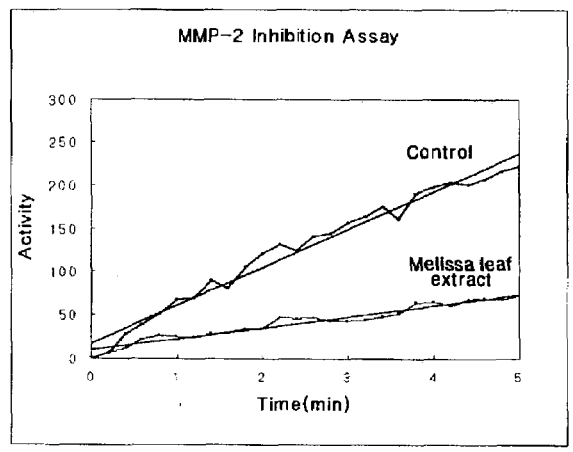
[FIG. 8]
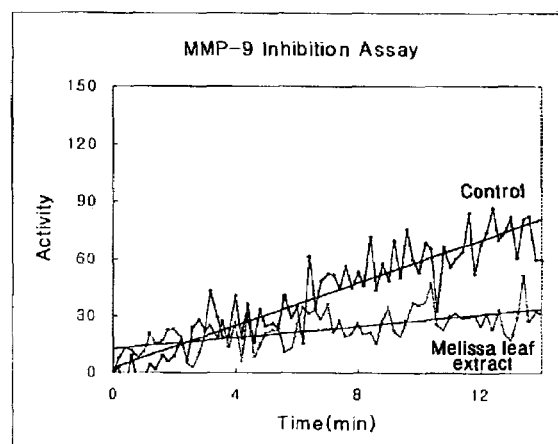

[FIG. 9]
A
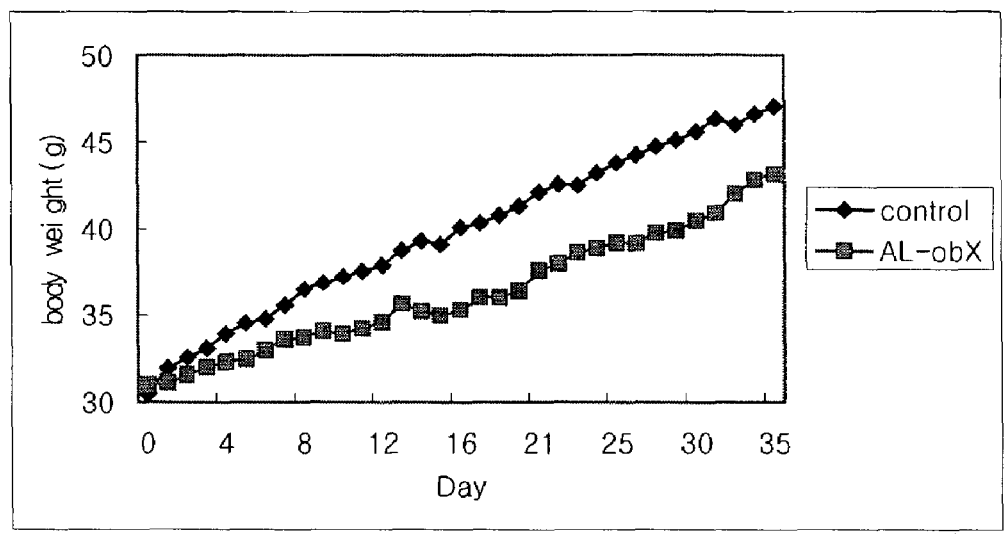
B
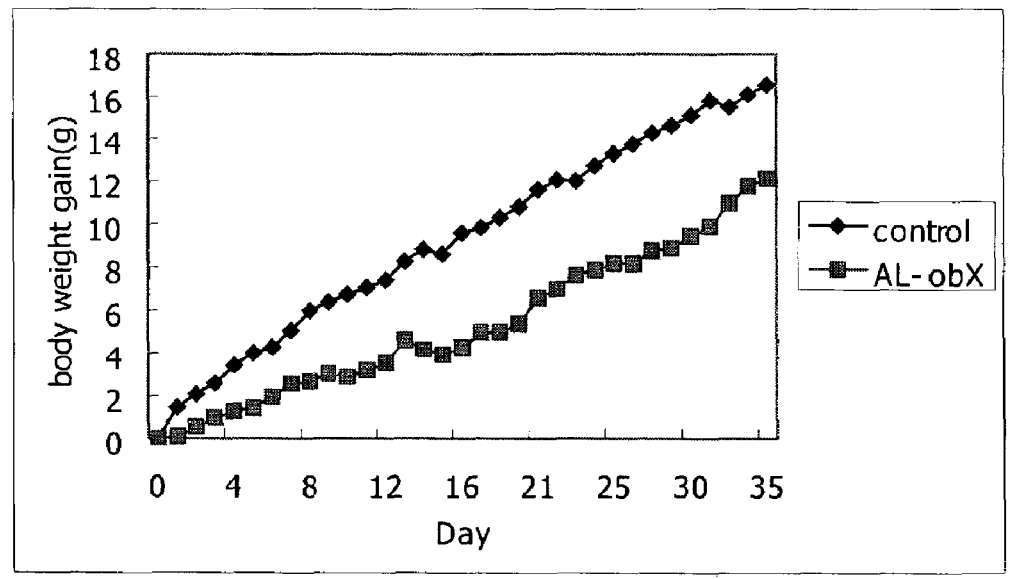

[FIG. 10]
A
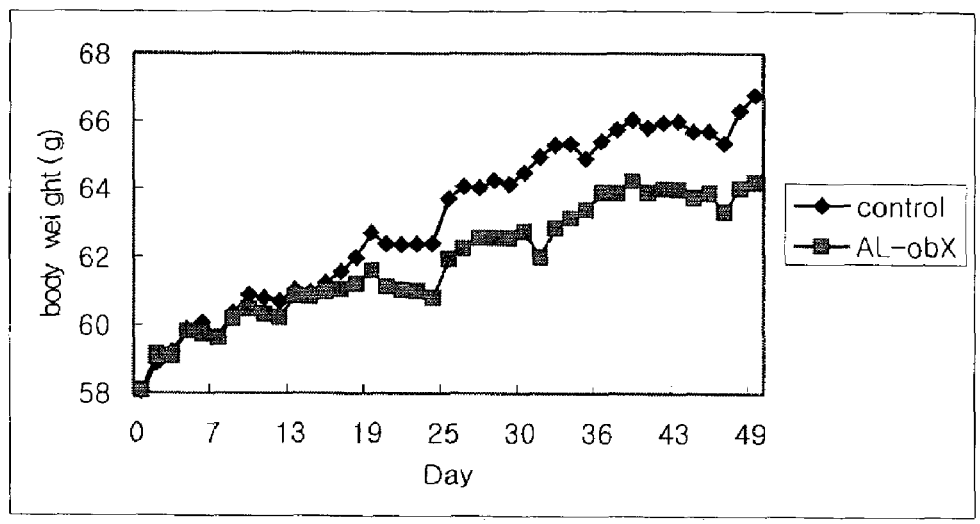
B
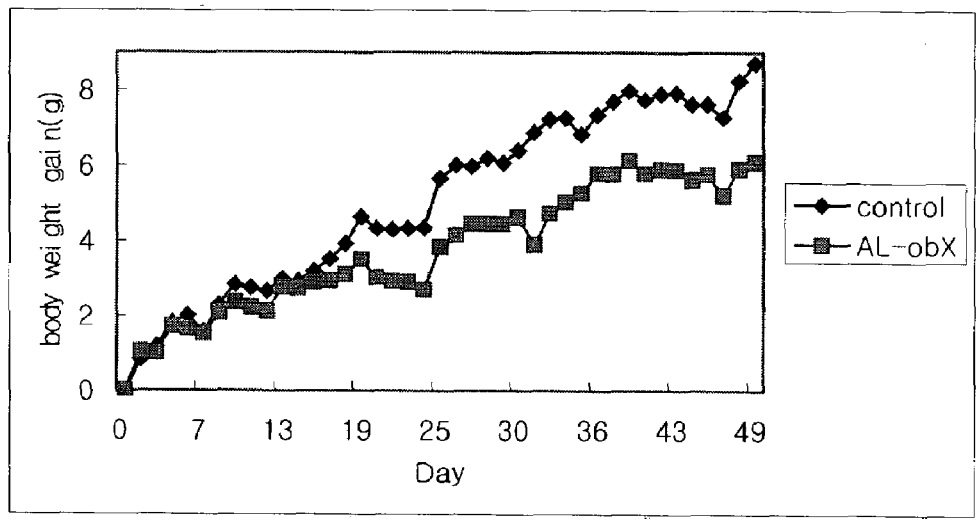

[FIG. 11]
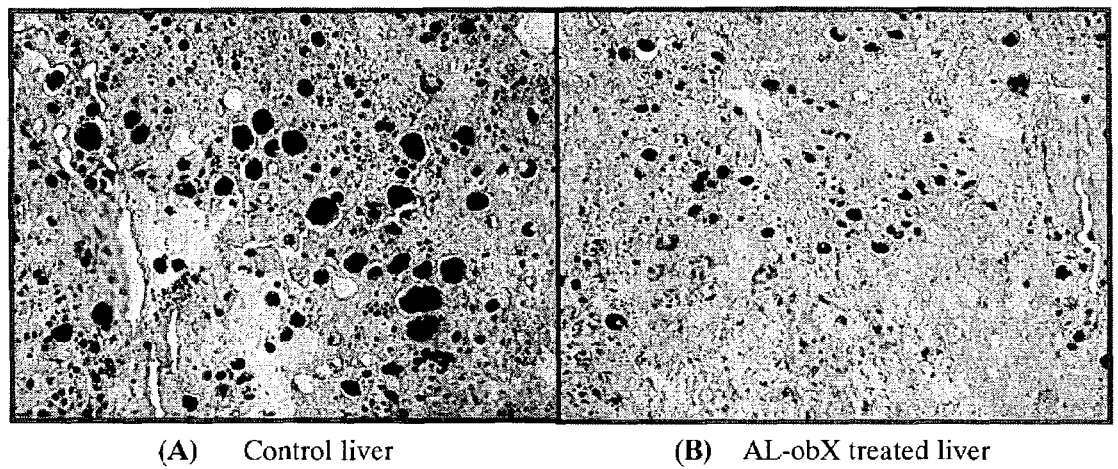
(A) Control liver  (B) AL-obX treated liver
[FIG. 12]
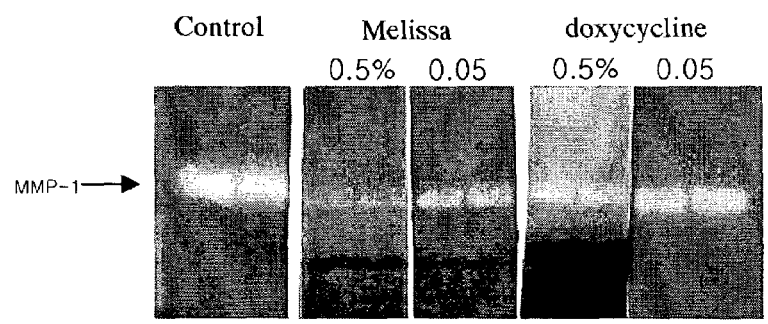

[FIG. 13]
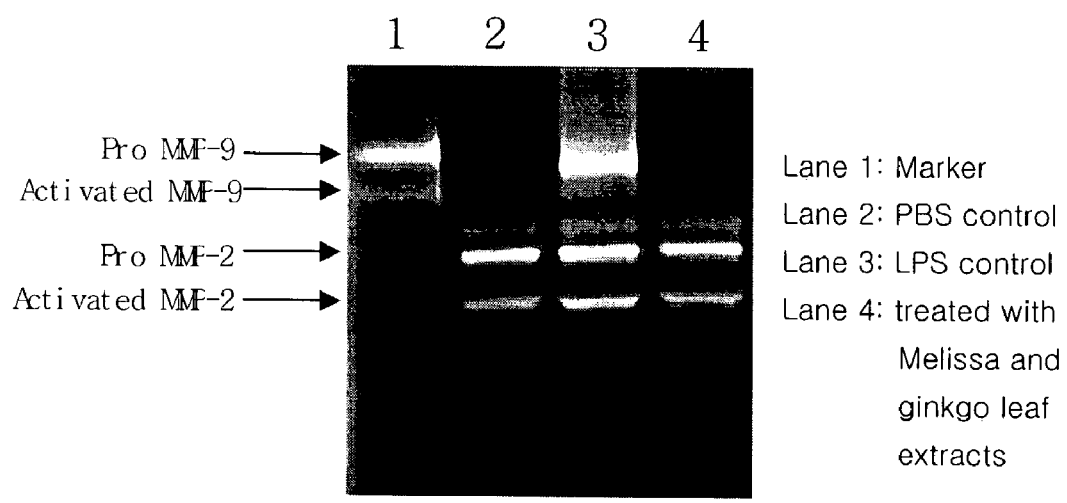

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Substrate for MMP-1 and MMP-9
<220> FEATURE:
<221> NAME/KEY: misc_feature
<222> LOCATION: (1)..(1)
<223> OTHER INFORMATION: Pro is 2,4-dinitrophenyl Pro.

<400> SEQUENCE: 1

Pro Leu Ala Leu Trp Ala Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Substrate for MMP-2
<220> FEATURE:
<221> NAME/KEY: misc_feature
<222> LOCATION: (1)..(1)
<223> OTHER INFORMATION: Pro is (7-methoxycoumarin-4-yl) acetyl Pro.
<220> FEATURE:
<221> NAME/KEY: misc_feature
<222> LOCATION: (4)..(4)
<223> OTHER INFORMATION: Leu is N-3-(2,4-dinitrophenyl)-L-2,3-
      diaminopropionyl Leu.
<220> FEATURE:
<221> NAME/KEY: misc_feature
<222> LOCATION: (6)..(6)
<223> OTHER INFORMATION: Arg is aminated.

<400> SEQUENCE: 2

Pro Leu Gly Leu Ala Arg
1               5
```

COMPOSITION COMPRISING *MELISSA* LEAF EXTRACT FOR ANTI-ANGIOGENIC AND MATRIX METALLOPROTEINASE INHIBITORY ACTIVITY

CROSS-REFERENCE TO RELATED APPLICATIONS

The present application is a continuation-in-part application claiming benefit of priority to PCT/KR01/02148, filed on Dec. 12, 2001, the contents of which are incorporated by reference herein in its entirety.

BACKGROUND OF THE INVENTION

1. Field of the Invention

The present invention relates to a composition comprising *Melissa* leaf extract having inhibitory activity on angiogenesis and matrix metalloproteinase. The present invention further relates to composition comprising *Melissa* leaf extract as active ingredient, which can be used as pharmaceuticals, food or cosmetics for treatment or prevention of angiogenesis- and/or MMP-dependent diseases.

2. General Background and State of the Art

*Melissa* (*Melissa officinalis*), a plant in a Labiatae family, is also called lemon balm, balm, or dropsy plant as common and folk names.

Some of the key constituents of *Melissa officinalis* extract are volatile oils (geranial, neral, citronellal, linalool, geraniol, geranylacetate, methyl citronellate, trans-beta-ocimene, germacren, eugenol), caffeic acid derivatives, flavonoids, triterpenes, catechins and tannins. Rosmarinic acid, a derivative of caffeic acid, is the most abundant component (about 4.7%) of the *Melissa* leaf extract, which is known to have anti-inflammatory activity.

*Melissa* is edible and medicinal. Fresh leaves can be added to salad and used to make sauces for fish, poultry and pork. Dried or fresh the whole plant is used to make cool refreshing drinks or warm relaxing teas, which is good for fevers, colds, and headache. As an alternative medicine, it is applied for calming nerves, relieving menstrual cramps, insomnia, depression, hyperthyroidism, upset stomach, and colic in babies. It is antibacterial, antispasmodic, antiviral, carminative, diaphoretic, digestive, emmenagogue, febrifuge, sedative, and tonic. *Melissa* leaf extract is also considered a blood circulation activator, which helps in dilation of peripheral blood vessels. Fresh crushed leaves are applied to wounds and insect bites. The oil from *Melissa* is often added to skin preparations and perfumes. The essential oil is also used in aromatherapy (Cohen R A, Kucera L S, Herrmann E C Jr., *Proc Soc Exp Biol Med* 117, 431-434, 1964; Kucera L S, Cohen R A and Herrmann E C Jr, *Ann. NY Acad Sci* 130, 474-82, 1965).

Angiogenesis is the process of generating new capillary blood vessels. This results from activated proliferation of pre-existing endothelial cells. Neovascularization is tightly regulated, and activation occurs only during embryogenic development, tissue remodeling, wound healing and periodic cycles of corpus luteum development (Folkman and Cotran, Relation of vascular proliferation to tumor growth, *Int Rev Exp Pathol* 16 207-248, 1976).

Endothelial cells grow very slowly as compared with other types of cells in the body. However, if the proliferation of these cells is induced by the failure of regulation of angiogenesis, some pathological status is developed (Timar, *J Pathol Oncol Res* 6, 85-94, 2001). Pathological angiogenesis is involved in many diseases. For example, cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are related to angiogenesis. Chronic inflammatory diseases such as arthritis, dermatological disease such as psoriasis, telangiectasis, pyogenic granuloma, seborrheic dermatitis and acne are also angiogenesis-dependent.

In particular, angiogenesis is essential to metastasis and growth of cancer (D'Amato R J and Adamis A P, *Ophthalmol* 102, 1261-1262, 1995; Arbiser J L, *J Am Acad Derm* 34, 486-497, 1996; O'Brien K. D. et al. *Circulation* 93, 672-682, 1996; Hanahan D and Folkman J, *Cell* 86, 353-364, 1996). New blood vessels provide not only nutrients and oxygen to fast-growing cancer cells, but also ways of entering the blood stream resulting in metastasis (Polverini P. J., *Critical Reviews in Oral Biology*, 6, 230-247, 1995). Currently, a large variety of chemotherapy and immunotherapy are applied in the treatment of cancer, but the efficacy of the therapies is limited and nothing can successfully extend the life of cancer patients, due to the lack of anti-metastasis effects.

Arthritis, a well-known inflammatory disease, is initiated as an autoimmune disease. However, the growth of vascular endothelial cell in the synovial cavity is activated by the inflammatory cytokines, which finally destroy cartilage in the articulation (Kocb A E, Polverini P J and Lcibovich S J, *Arth Rheum* 29, 471-479, 1986; Stupack D G, Storgard C M and Cheresh D A, *Braz J Med Biol Rcs* 32, 578-581, 1999; Koch A E, *Arthritis Rheum* 41, 951-962, 1998).

Many people are losing their eyesight all over the world because of various ocular diseases. Many patients become blind due to the infiltration of the capillary blood cells into the vitreous humor (Jeffrey M I and Takayuki A, *J Clin Invest* 103, 1231-1236, 1999).

Psoriasis is caused by extremely active proliferation of skin cells. Fast-growing cells requires sufficient blood supply, and angiogenesis is abnormally induced in psoriasis (Folkman J., *J Invest Dermatol* 59, 40-48, 1972).

As mentioned above, angiogenesis is closely related to initiation and progression of many diseases. Therefore, inhibitors of angiogenesis can be the good candidates for the treatment of those diseases. Many efforts have been made toward the development of angiogenesis inhibitors in order to prevent and/or treat those diseases.

Since the individual cells that make up even a single tumor vessel vary widely, the effectiveness of cancer treatments can be improved with various types of anti-angiogenic therapy. It is desirable to prepare a cocktail of several angiogenesis inhibitors for optimal anti-angiogenic therapy.

One of the major events for inducing angiogenesis is a breakdown of the extracellular matrix before the formation of the capillary blood vessels. The most important enzyme of matrix degradation is matrix metalloproteinase (MMP), a family of over 20 enzymes. MMPs are endopeptidase, which degrade or proteolyze the components of the extracellular matrix such as collagen, proteoglycan, and gelatin, and are classified into four groups: collagenase, gelatinase, stromelysin, and membrane-type MMP. Many enzymes in the MMP family have substrate specificity. The expression of MMP is induced under various physiological circumstances when remodeling of an extracellular matrix is required (Curry T E Jr, Osteen K G, *Biol Repord* 64, 1285-1296, 2001; Damjanovske S, Amano T, Li Q, Ueda S, Shi Y B, Ishizuya-Oka A, Ann NY Acad Sci 926, 180-191, 2000; Ravanti L, Kahari V M, Int J Mol Med 6, 391-407 2000).

Increased expression or activation of MMPs is observed in many pathological states, such as atherosclerosis, Alzheimer's disease, skin aging, wrinkle, arthritis, corneal ulcer, proteinuria, abdominal aortic aneurysm, regressive cartilage loss, myelinated nerve loss, liver fibrosis, nephroglomerular disease, germinal membrane ruptures, inflammatory bowel disease, gingivitis/periodontitis, senile macular degeneration, retinopathy, Sjogren syndrome, myopia, rejection of cornea implantation, angiogenesis and cancer metastasis. (Woessner Jr., *Annals NY Acad Sci*, 732, 11-21, 1994; Warner et al., *Am J Pathol*, 158, 2139-44, 2001; Stetler-Stevenson, *Surg Oncol Clin N Am*, 10, 383-92, 2001)

For example, stromelysins are known to be the major enzymes for disruption of cartilage (Murphy, G. et al., *Biochem J*, 248, 265-268, 1987). Collagenases, gelatinases and stromelysins are responsible for the degradation of the extracellular matrix in many types of retinopathies (Bruns, F. R. et al., *Invest Opthalmol and Visual Sci*, 32, 1569-1575, 1989). Collagenases and stromelysins are identified in fibroblast from gingiva in inflammation, and the activity of the enzyme is dependent on the degree of inflammation (Beeley, N. R. A. et al., supra; Overall, C. M. et al., *J Periodontal Res*, 22, 81-88, 1987).

Recent reports have also shown that MMP-1 activity is highly induced in Alzheimer's disease, and MMP-1 and MMP-3 are involved in the pathophysiology of the disease (Leake A, Morris C M, & Whateley, *J Neurosci Lett* 291, 201-3, 2000; Yoshiyama Y, Asahina M, & Hattori T, *Acta Neuropathol (berl)*, 99, 91-5, 2000).

MMPs are also responsible in solar UV radiation-induced skin damage, affecting skin tone and resiliency leading to premature aging. The symptoms of which include leathery texture, wrinkles, mottled pigmentation, laxity and sallowness. Therefore, MMP inhibitors could be included in cosmetics for anti-photoaging or anti-wrinkle agent (Hase T, Shinata K, Murase T, Tokimitsu I, Hattori M, Takimoto R, Tsuboi R and Ogawa H, *Br J Dermatol* 142, 267-273, 2000; Fisher G J, Talwar H S, Lin J, Voorhees J J, *Photochem Photobiol* 69, 154-157, 1999).

Since inhibitors for MMP and angiogenesis can be applied for treatment of many diseases, development of angiogenesis inhibitor as new drugs is expected. Desirable inhibitors should not have toxic or adverse effect with good patient compliance because inhibitors need to be administered for a long time.

SUMMARY OF THE INVENTION

The inventors have found that *Melissa* leaf extract exerts the following action: inhibition of angiogenesis, and inhibition of the proteolytic activity of matrix metalloproteinase Accordingly, the present invention provides an anti-angiogenic composition comprising *Melissa* leaf extract as active ingredient with or without other active ingredients.

More specifically, the present invention provides an anti-angiogenic composition for pharmaceutical, dietetic, or nutraceutical use.

Thus, the composition of the present invention can be used for the treatment or prevention of diseases derived from angiogenesis.

Further, the present invention provides an MMP-inhibitory composition comprising *Melissa* leaf extract as active ingredient with or without other active ingredients.

More specifically, the present invention provides an MMP-inhibitory composition for pharmaceutical, dietetic, nutraceutical, or cosmetic use.

Thus, the composition of the present invention can be used for the treatment or prevention of diseases derived from MMP activity.

These and other objects of the invention will be more fully understood from the following description of the invention, the referenced drawings attached hereto and the claims appended hereto.

The present invention is directed to a composition comprising *Melissa* leaf extract for inhibiting angiogenesis. The composition additionally comprises at least one ingredient selected from the group of *Ginkgo biloba* extract, ticlopidine, glucosamine, horse chestnut extract, *Glycyrrhiza glabra* extract, *Cinnamonum cassia* extract, *Sophora japonica* extract, *Atractylodes japonica* extract, *Atracylodes lancea* extract, *Artemisia capillaris* extract, *Morus alba* extract, *Houttuynia cordata* extract, *Lonicera japonica* extract, *Inula japonica* extract, *Inula britannica* extract, *Paeonia albiflora* extract, *Paeonia japonica* extract, *Paeonia obovata* extract, *Curcuma domestica* extract, *Curcuma longa* extract, *Saururus chinensis* extract, *Vaccinium myrtillus* extract, *Rubus* spp. extract, *Melilotus officinalis* extract, *Agelica gigantis* extract, *Salvia officinalis* extract, *Salvia miltorrhiza* extract, *Liriope platyphylla* extract, *Zingiber officinalis* extract, *Ulmus cavidiana* extract, *Ulmus macrocarpa* extract, *Camellia japonica* extract and *Vitis vinifera* extract. The composition may be a pharmaceutical composition for angiogenesis inhibition. The composition also may be a food composition for angiogenesis inhibition. The food composition may be a nutraceutical. The composition is also used for prevention and/or treatment of at least one disease selected from the group consisting of cancer metastasis, angioma, angiofibroma, diabetic retinopathy, premature infant's retinopathy, neovascular glaucoma, corneal disease induced by angiogenesis, involutional macula, macular degeneration, pterygium, retinal degeneration, retrolental fibroplasias, granular conjunctivitis, psoriasis, telangiectasis, pyogenic granuloma, seborrheic dermatitis, acne, and arthritis.

The present invention is also directed to a composition comprising *Melissa* leaf extract for inhibiting matrix metalloproteinase activity. The composition additionally comprises at least one ingredient selected from the group of *Ginkgo biloba* extract, ticlopidine, glucosamine, horse chestnut extract, *Glycyrrhiza glabra* extract, *Cinnamonum cassia* extract, *Sophora japonica* extract, *Atractylodes japonica* extract, *Atracylodes lancea* extract, *Artemisia capillaris* extract, *Morus alba* extract, *Houttuynia cordata* extract, *Lonicera japonica* extract, *Inula japonica* extract, *Inula britannica* extract, *Paeonia albiflora* extract, *Paeonia japonica* extract, *Paeonia obovata* extract, *Curcuma domestica* extract, *Curcuma longa* extract, *Saururus chinensis* extract, *Vaccinium myrtillus* extract, *Rubus* spp. extract, *Melilotus officinalis* extract, *Agelica gigantis* extract, *Salvia officinalis* extract, *Salvia miltorrhiza* extract, *Liriope platyphylla* extract, *Zingiber officinalis* extract, *Ulmus cavidiana* extract, *Ulmus macrocarpa* extract, *Camellia japonica* extract and *Vitis vinifera* extract. The composition may be a pharmaceutical composition for inhibiting matrix metalloproteinase activity. The composition may also be a food composition for inhibiting matrix metalloproteinase activity. The composition may further be a nutraceutical. The composition also may be a cosmetic composition for inhibiting matrix metalloproteinase activity. The composition may be used for treatment of at least one disease selected from the group consisting of cancer metastasis, atherosclerosis, restenosis, MMP-dependent osteopathy, inflammation of the central nervous system, Alzheimer's disease, skin aging, corneal ulcer, synechia, bone disease, proteinuria, abdominal aortic aneurysm, regressive cartilage loss, myelinated nerve loss, liver fibrosis, nephrogromerula disease, germinal membrane rupture, inflammatory bowel disease, gingivitis/periodontitis, senile macular degeneration, diabetic retinopathy, proliferate vitreous body retinopathy, immature retinopathy, eye inflammation, conical cornea, Sjogren syndrome, myopia, eye tumor, rejection in cornea implantation, rheumatoid arthritis, arthritis and septic arthritis.

The present invention is also directed to a method of inhibiting angiogenesis, comprising administering a composition comprising *Melissa* leaf extract to a subject. The composition may also comprise *Ginkgo biloba* extract. Further the composition may comprise ticlopidine.

The present invention is also directed to a method of reducing weight gain in a mammal, comprising administering to the mammal a composition comprising *Melissa* leaf extract. The composition may additionally comprise at least one ingredient selected from the group of *Ginkgo biloba* extract, ticlopidine, glucosamine, horse chestnut extract, *Glycyrrhiza glabra* extract, *Cinnamonum cassia* extract, *Sophora japonica* extract, *Atractylodes japonica* extract, *Atracylodes lancea* extract, *Artemisia capillaris* extract, *Morus alba* extract, *Houttuynia cordata* extract, *Lonicera japonica* extract, *Inula japonica* extract, *Inula britannica* extract, *Paeonia albiflora* extract, *Paeonia japonica* extract, *Paeonia ovovata* extract, *Curcuma domestica* extract, *Curcuma longa* extract, *Saururus chinensis* extract, *Vaccinium myrtillus* extract, *Rubus* spp. extract, *Melilotus officinalis* extract, *Agelica gigantis* extract, *Salvia officinalis* extract, *Salvia miltorrhiza* extract, *Liriope platyphylla* extract, *Zingiber officinalis* extract, *Ulmus cavidiana* extract, *Ulmus macrocarpa* extract, *Camellia japonica* extract and *Vitis vinifera* extract.

In addition, the present invention is also directed to a method of treating gum disease, such as periodontal disease or gingivitis comprising administering to a mammal suffering from the gum disease a composition comprising *Melissa* leaf extract. The composition may additionally comprise at least one ingredient selected from the group of *Ginkgo biloba* extract, ticlopidine, glucosamine, horse chestnut extract, *Glycyrrhiza glabra* extract, *Cinnamonum cassia* extract, *Sophora japonica* extract, *Atractylodes japonica* extract, *Atracylodes lancea* extract, *Artemisia capillaris* extract, *Morus alba* extract, *Houttuynia cordata* extract, *Lonicera japonica* extract, *Inula japonica* extract, *Inula britannica* extract, *Paeonia albiflora* extract, *Paeonia japonica* extract, *Paeonia obovata* extract, *Curcuma domestica* extract, *Curcuma longa* extract, *Saururus chinensis* extract, *Vaccinium myrtillus* extract, *Rubus* spp. extract, *Melilotus officinalis* extract, *Agelica gigantis* extract, *Salvia officinalis* extract, *Salvia miltorrhiza* extract, *Liriope platyphylla* extract, *Zingiber officinalis* extract, *Ulmus cavidiana* extract, *Ulmus macrocarpa* extract, *Camellia japonica* extract and *Vitis vinifera* extract.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1 is a picture showing the formation of tube by human umbilical vein endothelial cells (HUVEC) grown on Matrigel.

FIG. 2 is a picture showing HUVEC treated with 25 μg/ml of *Melissa* leaf extract.

FIG. 3 is a graph of effect of *Melissa* leaf extract on angiogenesis in mouse Matrigel model.

FIG. 4 is a graph showing the inhibition of angiogenesis by oral administration of *Melissa* leaf extract in mouse Matrigel model.

FIGS. 5A-B are pictures showing anti-angiogenic effect of *Melissa* leaf extract in chorioallantoic membrane assays (A: control, B: treated).

FIG. 6 is a graph showing inhibition of MMP-1 activity by *Melissa* leaf extract.

FIG. 7 is a graph showing inhibition of MMP-2 activity by *Melissa* leaf extract.

FIG. 8 is a graph showing inhibition of MMP-9 activity by *Melissa* leaf extract.

FIGS. 9A-B are graphs showing (A) body weight and (B) weight gain after 5 weeks of AL-obX treatment to 6-week-old ob/ob mice orally.

FIGS. 10A-B are graphs showing (A) body weight and (B) weight gain after 7 weeks of AL-obX treatment to 21-week-old ob/ob mice orally.

FIGS. 11A-B are pictures showing histology of liver stained with osmium tetroxide. Osmium tetroxide blacken lipid vacuoles in liver. A, control liver; B, liver treated with *Melissa* extract.

FIG. 12 is a casein zymogram showing inhibition of MMP-1 activity by *Melissa* and doxycycline.

FIG. 13 is a picture showing gelatin zymogram of gingival tissue extract of rat periodontitis model.

DETAILED DESCRIPTION OF THE PREFERRED EMBODIMENTS

In the present application, "a" and "an" are used to refer to both single and a plurality of objects.

As used herein, "angiogenesis" is meant the growth of a new blood vessel in which the proliferation and/or migration of an endothelial cell is a key step. By "inhibiting angiogenesis" or "anti-angiogenesis" is meant the inhibition of any of the steps of the process of angiogenesis that includes, without limitation, proliferation and/or migration of endothelial cells, and may include the inhibition of MMP activity.

As used herein, "angiogenesis related disease" refers to those diseases that are caused by the formation of excessive blood vessels.

As used herein, administration "in combination with" one or more further therapeutic agents includes simultaneous (concurrent) and consecutive administration in any order.

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "extract" refers to a concentrated preparation of the essential constituents of the medicinal plant. Typically, an extract is prepared by drying and powderizing the plant. Optionally, the plant, the dried plant or the powderized plant may be boiled in solution. The extract may be used in liquid form, or it may be mixed with other liquid or solid medicinal herbal extracts. Alternatively, the medicinal herbal extract may be obtained by further precipitating solid extracts from the liquid form.

In further detail and/or alternatively, "extract" refers to a concentrated preparation of the essential constituents of the medicinal plant. Typically, an extract is prepared by drying and subsequently cutting or grinding the dried material. The extraction process may then be performed with the help of an appropriate choice of solvent, typically water, ethanol, ethanol/water mixture, methanol, butanol, iso-butanol, acetone, hexane, petroleum ether or other organic solvents by means of maceration, percolation, repercolation, counter-current extraction, turbo-extraction, or by carbon-dioxide hypercritical (temperature/pressure) extraction. The extract may then be further evaporated and thus concentrated to yield a soft extract (extractum spissum) and/or eventually a dried extract, extracum siccum, by means of spray drying, vacuum oven drying, fluid-bed drying or freeze-drying.

The herbal composition may be made by drying and grinding various herbs, such as chosen from *Ginkgo biloba*, horse chestnut, *Glycyrrhiza glabra*, *Cinnamonum cassia*, *Sophora japonica*, *Atractylodes japonica*, *Atracylodes lancea*, *Artemisia capillaris*, *Morus alba*, *Houttuynia cordata*, *Lonicera japonica*, *Inula japonica*, *Inula britannica*, *Paeonia albiflora*, *Paeonia japonica*, *Paeonia obovata*, *Curcuma domestica*, *Curcuma longa*, *Saururus chinensis*, *Vaccinium myrtillus*, *Rubus* spp., *Melilotus officinalis*, *Agelica gigantis*, *Salvia officinalis*, *Salvia miltorrhiza*, *Liriope platyphylla*, *Zingiber officinalis*, *Ulmus cavidiana*, *Ulmus macrocarpa*, *Camellia japonica* and *Vitis vinifera*. Most preferably, all of the herbs and other compositions are used together in various ratios. But it is understood that not all of these herbs or compositions may be necessary for the desired effect of inhibiting angiogenesis in a patient. Any combination of these herbs may be used so long as the composition inhibits MMP and/or inhibits angiogenesis in the patient when administered to the patient. Preferably, *Melissa* extract is present in at least about 0.1 to 99% by weight of the total weight of the herbal composition. Preferably, the composition comprises 0.5% by weight of the *Melissa* extract composition. Still preferably, the amount may be at least about 2%, 3%, 5%, 10%, 20%, 30%, 40%, 50%, 60%, 70%, 80%, 90%, 95%, or 100% of the total weight. The amount of *Melissa* extract may vary depending on the uses of the composition. For instance, in a cosmetic formulation, the amount of *Melissa* extract may preferably comprise from about 0.5% to about 5% of the total weight of the composition. However, in a food formulation, such as nutraceutical composition, the amount of incorporated *Melissa* extract may be higher and preferably may be greater than about 10% of the total weight.

As used herein, a "dose" refers to a specified quantity of a therapeutic agent prescribed to be taken at one time or at stated intervals.

It will be readily apparent that all of the above compositions in their alternate forms may be used alone or in combination to provide an anti-angiogenic herbal medicine, which when administered to a patient, results in angiogenesis preventive or therapeutic effect.

Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions will include a conventional carrier or vehicle and, in addition, may include other medicinal agents, pharmaceutical agents, carriers, adjuvants, and so on. In the invention, the carrier for the herbal composition may preferably include, a base of berries or fruit, a base of vegetable soup or bouillon, a soya-milk drink, or a nutritive supplement.

If a vegetable soup or bouillon base is desired to be used as a base for the herbal composition, it can be readily seen that any vegetable soup or bouillon base can be used, so long as the anti-angiogenic effect of the herbal composition is maintained.

If it is desired that the base be made from extracts of berries or fruits, then it is understood that any berry or fruit base may be used so long as its use does not interfere with the anti-angiogenic effectiveness of the herbal medicinal composition.

If the inventive composition is desired to be placed into a soya milk, it is understood that such a drink will need to be refrigerated to prevent toxic effects. It is further understood that the inventive composition may be placed, mixed, added to or combined with any other nutritional supplement so long as the anti-angiogenic effect of the herbal composition is maintained.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, and so on.

The amount of the herbal medicine in a formulation can vary within the full range employed by those skilled in the art, e.g., from about 0.01 weight percent (wt %) to about 99.99 wt % of the medicine based on the total formulation and about 0.01 wt % to 99.99 wt % excipient.

The preferred mode of administration, for the conditions mentioned above, is oral administration using a convenient daily dosage regimen, which can be adjusted according to the degree of the complaint. For said oral administration, a pharmaceutically acceptable, non-toxic composition is formed by the incorporation of the herbal composition in any of the currently used excipients, such as, for example, pharmaceutical grades of dextrin, mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

In one embodiment, the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyrrolidone, acacia gum, gelatin, cellulose and derivatives thereof, and the like.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active composition may be incorporated into sustained-release preparations and formulations.

It is understood that by "pharmaceutical composition" or "herbal composition", it is meant that the herbal composition is formulated into a substance that is to be administered purposefully for treating or preventing angiogenesis related disease in an individual. However, it is understood that the herbal composition per se will not have a toxic effect.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "nutraceutical" is a combination of "nutritional" and "pharmaceutical" and refers to food or food component that act as medicines. Nutraceuticals or "functional foods" are a crude or refined specific food source that allows concentrated food therapy in a specific area of nutrition. These foods assist in the prevention or treatment of disease. Nutraceuticals may further refer to natural products that are used to supplement the diet by increasing the total dietary intake of important nutrients. Typically, nutraceuticals derived from botanical preparations such as *Melissa* leaf extracts are as crude forms, powders or extracts, and may used in the form of for example beverages made with herbal products and other ingredients.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

*Melissa* Leaf Extract

The present invention relates to treatment for various diseases that are related to angiogenesis. In this way, the inventive therapeutic composition may be administered to human patients who are either suffering from, or prone to suffer from the disease by providing compositions that inhibit angiogenesis. In particular, the disease is associated with cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis and chronic inflammatory diseases such as arthritis, dermatological disease such as psoriasis, telangiectasis, pyogenic granuloma, seborrheic dermatitis and acne.

In another embodiment, the present invention relates to treating various diseases that are characterized by excessive angiogenesis, which include but are not limited to, cancer, atherosclerosis, rheumatoid arthritis, endometriosis, ocular disease or obesity.

The formulation of therapeutic compositions is generally known in the art and reference can conveniently be made to Remington's Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation.

The inventors have found that *Melissa* leaf extract of this invention inhibits angiogenesis not only in tube formation assay, but also in CAM assay and mouse Matrigel model. *Melissa* leaf extract also inhibits angiogenesis when it is orally administered.

The tube formation assay is an in vitro experimental method that is closely related to in vivo efficacy, and this assay investigates the effect on the migration and differentiation of human endothelial cell forming microvascular network. While the CAM assay is an in vivo assay using fertilized eggs, angiogenesis can be quantitatively measured in mouse Matrigel model.

Further, the inventors have found that *Melissa* leaf extract inhibited MMP, a family of essential enzymes for angiogenesis and cancer metastasis. When the effect of *Melissa* leaf extract on MMPs is investigated with MMP-1, MMP-2, and MMP-9, it drastically inhibits activity of all three enzymes. The inhibitory effect of *Melissa* leaf extract on MMPs is not, however, limited to these three enzymes.

It is therefore clear that the composition comprising *Melissa* leaf extract of the present invention is used as an anti-angiogenic agent for the treatment or prevention of angiogenesis-dependent diseases, for pharmaceutical, nutraceutical, or dietetic use.

It is therefore also clear that the composition comprising *Melissa* leaf extract of the present invention is used as an MMP-inhibitory agent for the treatment or prevention of MMP-related diseases, for pharmaceutical, dietetic or cosmetic use.

*Melissa* leaf extract used in the present invention can be purchased or prepared with conventional methods. Commercially available *Melissa* leaf extract or *Melissa* leaf extract powder may also be used. An example of a conventional extraction method is as follows.

In brief, 10 to 20 L of an aqueous water or alcohol (for example, methanol, ethanol, butanol, etc.) or acetone is added to 1 kg of dried *Melissa* leaves. The mixture is allowed to extract at a temperature ranging from 60 to 80° C., for a period ranging from 30 min to 2 hours. The extraction process may be repeated 2 to 3 times with other solvents (chloroform, ethyl acetate, ketone, etc.). The resulting extract is concentrated to obtain a *Melissa* leaf extract.

As mentioned above, *Melissa* leaf extract of the present invention has inhibitory effects on angiogenesis and MMP activity. While MMPs are enzymes responsible for angiogenesis, anti-angiogenic activity of *Melissa* leaf extract is not limited to MMP inhibitory activity. That is, though MMPs are one of the factors for inducing angiogenesis, *Melissa* leaf extract can inhibit other factors of angiogenesis. Furthermore, the inhibitory of activity of *Melissa* leaf extract on MMP is not limited to inhibition of angiogenesis.

The composition of the present invention comprising *Melissa* leaf extract may also comprise more than one component of other angiogenesis inhibitors, such as ticlopidine, glucosamine (2-amino-2-deoxy-D-gucopyranose), horse chestnut extract and *Ginkgo biloba* extract for the prevention and/or treatment of angiogenesis- and MMP-dependent diseases. We have previously reported that angiogenesis is inhibited by commercially available pharmaceutical composition such as horse chestnut extract (KR10-2001-66246), glucosamine and its salt (KR-10-2001-18675), *Ginkgo biloba* extract (KR10-2000-45265) and ticlopidine (KR10-2000-43589).

These commercially available drugs can be co-treated with *Melissa* leaf extract of present invention to potentate the effect of the composition.

Specifically, combined treatment of *Melissa* leaf extract with *Ginkgo biloba* extract or ticlopidine can be used as metastasis inhibitors.

The composition of the present invention comprising *Melissa* leaf extract may also comprise more than one component of other anti-cancer, anti-inflammatory and anti-aging agents such as *Glycyrrhiza glabra*, *Cinnamonum cassia*, *Sophora japonica*, *Atractylodes japonica*, *Atracylodes lancea*, *Artemisia capillaris*, *Morus alba*, *Houttuynia cordata*, *Lonicera japonica*, *Inula japonica*, *Inula britannica*, *Paeonia albiflora*, *Paeonia japonica*, *Paeonia obovata*, *Curcuma domestica*, *Curcuma longa*, *Saururus chinensis*, *Vaccinium myrtillus*, *Rubus* spp., *Melilotus officinalis*, *Agelica gigantis*, *Salvia officinalis*, *Salvia miltorrhiza*, *Liriope platyphylla*, *Zingiber officinalis*, *Ulmus cavidiana*, *Ulmus macrocarpa*, *Camellia japonica* and *Vitis vinifera*. Above compositions can be added to drugs, quasi-drugs, foods or beverages used for anti-angiogenic purpose.

The anti-angiogenic activity of above component is also confirmed by tube formation of HUVEC as previously mentioned. The inhibition of tube formation by 50 µg/ml of each composition was 30-100% as compared with non-treated control HUVEC. For example, percent inhibition was 100% for *Cinnamonum cassia*, 51.7% for *Atractylodes japonica*, 53% for *Artemisia capillaris*, 53% for *Morus alba*, 40% for *Vaccimium myrtillus*, 30% for *Houttuynia cordata*, and 38% for *Paeonia japonica*.

A composition comprising *Melissa* leaf extract can also comprise more than one kind of diluent including dextrose, maltodextrin, saline, buffered saline, water, glycerol, and ethanol, but the diluent is not limited. Appropriate diluents are listed in the written text of Remington's Pharmaceutical Science (Mack Publishing co, Easton Pa.).

Formulations containing *Melissa* leaf extract may be prepared in any form. The formulation can be prepared as injectable preparation (true solution, suspension, or emulsion) and preferably in oral dosage form (tablet, capsule, soft capsule, aqueous medicine, pill, granule) and topical preparation (ointment, patch, spray, solution, and the like).

The composition comprising *Melissa* leaf extract of the present invention can be administered by various routes. The route of administration includes oral, intravenous, intraperitoneal, subcutaneous, intramuscular, intra-arterial, transdermal, rectal, nasal, ocular, and topical application.

The composition comprising *Melissa* leaf extract of the present invention may be applied differently according to the diseases and route of administration. It should be understood that the amount of active ingredient has to be determined with various factors. These factors include the severity of the patient's symptoms, other co-administered drugs (e.g., chemotherapeutic agents), age, sex, body weight of the individual patient, food, dosing time, the chosen route of administration, and the ratio of the composition.

A daily dose of *Melissa* leaf extract is preferable from about 5 mg to 2 g, most preferably 10 to 1000 mg. In general, 0.1 to 200 mg/kg of *Melissa* leaf extract can be administrated in a single dose or 2-3 divided doses per day.

The cosmetic composition comprising *Melissa* leaf extract of the present invention can be used for photoaging or wrinkle treatment.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

*Melissa* leaf extract was purchased from Emil Flachsmann AG and used in the following examples.

TEST 1—Effect of *Melissa* Leaf Extract on Tube Formation of HUVEC

The effect of *Melissa* leaf extract on angiogenesis was investigated in vitro with human endothelial cells.

To perform the tube formation assay, human umbilical vein endothelial cells (HUVEC) were isolated from freshly obtained cords after cesarean section. Cells were cultured and identified by immunocytochemical staining with anti-Factor VIII antibody. HUVEC grown on Matrigel (BD Bioscience, Bedford, Mass., USA), were treated with 25 µg/ml of the above *Melissa* leaf extract (Emil Flachsmann AG), and further incubated at 37° C. for 8-16 hrs. As a control, the procedure was repeated without *Melissa* leaf extract.

FIG. 1 shows that a tubular network is formed as a process of neovascularization, when they are grown on Matrigel. However, the microvascular network of HUVEC on Matrigel was disconnected by *Melissa* leaf extract as shown in FIG. 2.

FIG. 2 shows HUVEC grown on Matrigel treated with 25 µg/ml of *Melissa* leaf extract, which shows that the microvascular network was disconnected.

The area of the tube was determined by the image analysis program Image-Pro Plus® (Media Cybernetics, USA), and is summarized in Table 1. Tube formation after treatment of *Melissa* leaf extract was inhibited by about 66% as compared with the untreated control.

TABLE 1

| | Area of tube | % |
|---|---|---|
| Control | 11.56 | 100 |
| Melissa leaf extract | 3.92 | 34 |

TEST 2—Animal Experiment for Angiogenesis (Mouse Matrigel Model)

The anti-angiogenic activity of *Melissa* leaf extract was quantitatively investigated in mouse Matrigel model.

A 0.4 ml portion of Matrigel mixed with each of 50 ng/ml of basic fibroblast growth factor (bFGF) and 50 units/ml of heparin was implanted to C57BL/6 female mice of 6 to 8 week-old by subcutaneous injection. After 3-5 days, Matrigel was removed from excised skin of each mouse, the level of hemoglobin (Hb) in the Matrigel was measured with a Drabkin kit (Sigma Chemical Co., St. Louise, Mich., USA, Cat. No. 525), a reagent for determination of total hemoglobin in blood. The same experiment was done with Matrigel containing *Melissa* leaf extract (0.5 mg), and hemoglobin content of the treated group was compared with that of the control group. As shown in FIG. 3 and Table 2, the hemoglobin content of the treated group was remarkably reduced as compared with that of the control group. Therefore, angiogenesis was inhibited by about 99%.

TABLE 2

|  | Hemoglobin (g/dL) |
| --- | --- |
| Control | 453 ± 446 |
| Melissa leaf extract | 3 ± 7 |

In order to test the activity of orally administered *Melissa* leaf extract on angiogenesis, the following experiment was undertaken.

A 0.4 ml portion of Matrigel containing 50 ng/ml of basic fibroblast growth factor (bFGF) and 50 units/ml of heparin was implanted by subcutaneous injection, and 0.6 mg of *Melissa* leaf extract per mouse was orally administered twice a day for 4 days. At day 5, the Matrigel was removed and the amount of hemoglobin in the Matrigel was determined.

As shown in FIG. 4 and Table 3, the *Melissa* leaf extract-treated group showed a lower level of hemoglobin in Matrigel, about 71% of that of the control group. Therefore, *Melissa* leaf extract also showed anti-angiogenic activity when it was administered orally.

TABLE 3

|  | Hemoglobin (g/dL) |
| --- | --- |
| Control | 109 ± 198 |
| Melissa leaf extract | 32 ± 38 |

TEST 3—Angiogenesis Assay with Chorioallantoic Membrane Assays (CAM Assay)

Fertilized chicken eggs were kept in a humidified incubator at 37° C. After incubation for three days, 2-3 ml of albumin was aspirated from the eggs with a syringe of 26-gauge needle and the egg was sealed with transparent tape. A window of a small hole was drilled at the end of the eggs. Two days later, an aliquot of 50 μg of *Melissa* leaf extract dissolved in 15 μl of saline was applied to sterile Thermanox discs (Miles Scientific) and allowed to air dry. The discs were applied to the chorioallantoic membrane surface through the window and covered with transparent adhesive tape. The embryos were incubated for further three days at 37° C. in a humidified incubator. An appropriate volume of lipid emulsion was injected into the embryo chorioallantois using a 26-gauge needle so that the vascular network of the chorioallantoic membrane stood out against the white lipid background. As a control, 15 μl of physiological saline was loaded to a disc instead of *Melissa* leaf extract following the same procedure as mentioned above. The resulting blood vessels were observed and compared with treated eggs.

In the control group (n=20), capillary vessel formation was not affected in 90% of the embryo (FIG. 5A), while the inhibition of vessel formation in the disc (brighter part of the picture) treated with *Melissa* leaf extract was significant and the inhibition of the blood vessel formation of the chorioallantois was observed in all the treated eggs (n=15, 100%, FIG. 5B).

TEST 4—Effect of Combined Treatment of *Melissa* Leaf Extract with *Ginkgo biloba* Extract on Angiogenesis Inhibition The effect of co-treatment of *Melissa* leaf extract with other composition on angiogenesis was investigated in mouse Matrigel model.

A 0.4 ml portion of Matrigel containing 50 ng/ml of basic fibroblast growth factor (bFGF) and 50 units/ml of heparin was implanted by subcutaneous injection, and 1.0 mg of *Melissa* leaf extract combined with 0.5 mg of *Ginkgo biloba* extract was orally administered twice per day for 4 days.

Lower dose of combined composition of *Melissa* leaf extract with *Ginkgo biloba* extract were also given to mice in another group, which were taken one fifth of the previous amount of combined composition (0.2 mg of *Melissa* with 0.1 mg of *Ginkgo*).

The amount of hemoglobin in the Matrigel was determined and the result was compared with the non-treated control group. As summarized in Table 4, the average of total hemoglobin levels in the Matrigel from treated group were about 10-18% of that of the control group. The percent inhibition of angiogenesis by combined treatment was 82-90%, which was greater than the *Melissa* leaf extract alone.

TABLE 4

| Treatment | Hemoglobin (g/dL) | Inhibition (%) |
| --- | --- | --- |
| Control | 162 ± 174 | 0 |
| Melissa (1.0 mg) + Ginkgo (0.5 mg) | 29 ± 28 | 90 |
| Melissa (0.2 mg) + Ginkgo (0.1 mg) | 17 ± 19 | 82 |

TEST 5—Inhibition of Cancer Metastasis by Combined Treatment of *Melissa* Leaf Extract with Other Composition B16BL6 cells (5×10⁴) were injected into C57BL/6 male mouse of 6 to 7 weeks old through the tail vein. After that, 0.2 ml of water or drug combinations was daily given to mice by oral administration for 3 weeks. Three weeks after injection, the mice were sacrificed and the number of tumor colonies on the surface of lungs was counted under microscope. The average number of melanoma colonies in lungs from mice of treated group was less than that from control mice. The percent inhibition of metastasis is 37-38% in single drug treated groups, while it was reduced to 50-54% in combined treatment groups (Table 5).

That is, the combined treatment of *Melissa* leaf extract with other angiogenesis inhibitor is more potent than *Melissa* leaf alone.

TABLE 5

| Preparation | Colonies in lung | Inhibition (%) |
| --- | --- | --- |
| Control | 133 ± 39 | 0 |
| Melissa leaf extract | 84 ± 24 | 37 |
| Ginkgo biloba extract | 82 ± 21 | 38 |
| Ticlopidine | 83 ± 20 | 38 |
| Melissa + Ginkgo | 61 ± 15 | 54 |
| Melissa + ticlopidine | 67 ± 17 | 50 |

Example 2

(1) Preparation of MMP

MMP-1, MMP-2, and MMP-9 were cloned and prepared from insect cells (Sf21 insect cell) using Baculovirus system.

MMP-2 cDNA (GENEBANK No. XM_048244) was cloned to a pBlueBac4.5 transfer vector (Invitrogen, Cat no. V1995-20), and then transfected to Sf21 cells with Bac-N-Blue Transfection Kit (Invitrogen, Cat no. K855-01). Sf21 cells were incubated with TNM-FH (Sigma, St. Louis, Mo., U.S.A) media containing 10% fetal bovine serum at 27° C., then harvested and re-suspended at a concentration of $10^7$ cell/ml. The cell suspension was incubated with a virus containing the cloned gene for 1 hr at room temperature. Infected Sf21 cells were grown for 72 hrs and the medium was recovered. MMP-2 was purified with a gelatin-sepharose affinity column from the recovered medium.

MMP-1 (GENEBANK NO. XM_040735) and MMP-9 (GENEBANK NO. XM_009491) were prepared from corresponding genes as previously described. MMP-1 was purified with SP-sepharose, and MMP-9 was purified by gelatin-sepharose affinity chromatography.

(2) Inhibition of MMP Activity

In order to investigate MMP inhibition by *Melissa* leaf extract, MMP enzyme activity was assayed by a spectrofluorometric method (Perkin-Elmer LS50B).

Purified MMP-1, MMP-2, and MMP-9 were used after activation with 1 mM APMA before assay.

The substrate for MMP-1 and MMP-9 was 2,4-dinitrophenyl-Pro-Leu-Ala-Leu-Trp-Ala-Arg (SEQ ID NO:1), and Mca-Pro-Leu-Gly-Leu-Dap(Dnp)-Ala-Arg-NH$_2$ (SEQ ID NO:2:BACHEM, Cat. No. M-1895) was used as a substrate for MMP-2.

As a control, 10 nM MMP-1 and 1 μM substrate (SEQ ID NO:1) were mixed in 2 ml of reaction buffer (50 mM Tricine (pH 7.5), 10 mM CaCl$_2$, 200 mM NaCl) in a 2 ml cuvette. Fluorescence intensity was measured every 2 min for 20 min at room temperature with a spectrofluorometer under an excitation wavelength of 280 nm and an emission wavelength of 360 nm.

*Melissa* leaf extract (25 μg/ml) dissolved in water and 10 nM MMP-1 was added to a reaction buffer containing a substrate, and fluorescence intensity was measured in the same manner.

Activity for MMP-2 or MMP-9 was also assayed, and fluorescence intensity was measured as previously mentioned.

FIGS. 6, 7 and 8 are diagrams of activity of MMP-1, MMP-2, and MMP-9. As shown in FIG. 6, 57% of MMP-1 activity was inhibited by *Melissa* leaf extract. The inhibition of MMP-2 and MMP-9 by *Melissa* leaf extract was 71% (FIG. 7) and 73% (FIG. 8), respectively.

As previously mentioned, *Melissa* leaf extract of the present invention inhibits angiogenesis and matrix metalloproteinase activity. Based on that, *Melissa* leaf extract can be used as a new composition for treatment or prevention of angiogenesis- and/or MMP-dependent diseases.

Example 3

Male ob/ob mice(B6.V-Lep<ob>) were purchased from The Jackson Laboratory. This strain develops spontaneous obesity and rapidly accumulates adipose tissue. Anti-obesity composition (AL-obX) containing melissa leaf extract was dissolved in water and administered orally to six-week-old ob/ob mice at 125 mg/kg per day for 35 days. AL-obX was also administered orally to twenty-one-week-old ob/ob mice at 500 mg/kg per day for 49 days. Controls were received water vehicle orally. We measured body weights everyday. After 5 or 7 weeks, the mice were anesthetized by intraperitoneal injection of 2,2,2-Tribromoethanol and blood was collected for measuring glucose level. Gonadal fat pad was removed and subcutaneous fat pad were removed by dissecting from its attachment at the posterior iliac crest to the skin. The intestinal fat was also removed from the intestine. The weight of fat was determined. Portions of liver were fixed in 4% glutaraldehyde and then the tissue was stained with 2% osmium tetroxide for histology.

When AL-obX was administered to six-week-old ob/ob mice at 125 mg/kg per day for 35 days AL-obX treated mice were different from the control mice with respect to body weight (43.1±4.17 versus 47.0±3.85 g, respectively), weight gain (12.1±3.01 versus 16.6±2.24 g, respectively), gonadal fat mass (3.01±0.37 versus 3.24±0.23 g, respectively), subcutaneous fat (0.87±0.12 versus 1.02±0.15 g, respectively). Weight gain and adipose tissue weight including subcutaneous and gonadal fat in AL-obX treated mice were significantly less than controls (FIG. 9 and Table 6).

TABLE 6

|  | AL-obX | Control | % Decrease |
|---|---|---|---|
| Body weight (g) | 43.1 ± 4.17 | 47.0 ± 3.85 | 8 |
| Weight gain | 12.1 ± 3.01 | 16.6 ± 2.24 | 27 |
| Gonadal fat | 3.01 ± 0.37 | 3.24 ± 0.23 | 7 |
| Subcutaneous fat | 0.87 ± 0.12 | 1.02 ± 0.15 | 15 |

When the twenty-one-week-old ob/ob mice were treated with AL-obX at a dose of 500 mg/kg per day for 49 days body weight gain and adipose tissue weight were much lower than control mice (FIG. 10 and Table 7). Subcutaneous and intestinal fat were significantly decreased in AL-obX treated mice.

TABLE 7

|  | AL-obX | Control | % Decrease |
|---|---|---|---|
| Blood Glucose (mg/dl) | 178.6 ± 33.8 | 188.2 ± 20.9 | 5 |
| Body weight (g) | 63.9 ± 3.16 | 67.6 ± 2.44 | 5 |
| Weight gain (g) | 6.10 ± 0.8 | 9.16 ± 0.9 | 33 |
| Gonadal fat (g) | 1.63 ± 0.2 | 1.83 ± 0.2 | 11 |
| Subcutaneous fat (g) | 4.68 ± 0.6 | 5.36 ± 0.8 | 13 |
| Intestinal fat (g) | 1.52 ± 0.1 | 1.75 ± 0.2 | 13 |

The size and number of black lipid vacuoles in liver stained by osmium tetroxide were also significantly decreased in AL-obX treated mice compared with controls (FIG. 11), suggesting that adipose cells were sensitive to angiogenesis inhibitors, especially MMP inhibitors.

Example 4

Periodontal disease affects the gums, teeth and the bone support. And periodontitis is the most common cause of adult tooth loss. Activity of matrix metalloproteinases (MMP) such as MMP-1, -13, -9 in the periodontal tissue is highly induced in periodontitis as a response to persistent bacterial infection. Collagenases(MMP-1, -8, -13) play major role in destruction of type I collagen matrix of periodontal ligaments and alveolar bone, that results in deeper pockets and bone loss.

Therefore, MMP inhibitors may be applied for periodontal disease to stop further damage and progression of the disease by blocking the breakdown of tissue and bone.

*Melissa* leaf extract at the concentration of 25 μg/ml inhibited not only MMP-1 and MMP-9 but also MMP-8, and MMP-13 by 52%, and 61% respectively by spectrofluorometric method. The inhibitory activity of *Melissa* leaf extract was compared with doxycycline, well-known commercial MMP inhibitor in casein zymogram. As shown in FIG. 12, inhibitory effect of *Melissa* leaf extract on MMP-1 (collagenase-1) activity is greater than that of doxycycline.

Experimental Periodontitis was induced in adult male Sprague-Dawley rats (350-370 g) by injecting LPS endotoxin (Sigma Chemical). Under anesthesia each rat received three injections given every other day at 3 injection sites per animal. Injections were made into the anterior maxillary labial and palatal incisor gingivae. For control groups gingiva were injected with PBS or LPS and each rat was orally administered with vehicle, saline alone. For treatment group gingiva were injected with LPS and each rat was orally administered with saline containing 25 mg/kg of *Melissa* extract and 25 mg/kg of *Ginkgo* extract daily.

On day 7, after euthanasia the gingival tissues from the anterior maxillary labial and palatal incisor gingivae were removed to measure the MMP activity. 100 mg of the gingival tissues were extracted with 5 ml of 5M urea buffer at 4° C. and the extract was concentrated with Amicon Ultra centrifugal filter (MW cut off 10,000, Millipore) for gelatin zymogram analysis. As shown in FIG. 13, oral administration of both *Melissa* leaf extract and ginkgo biloba leaf extract reduced proMMP-9 which was highly increased in LPS-induced periodontitis gingivae. The total MMP activities were analysed by image analysis program Gel-Pro Plus (Media Cybernetics, USA) and summarized in Table 8. Total MMP activities were decreased by oral administration of *Melissa* leaf and *Ginkgo* leaf extract. Therefore, the composition containing *Melissa* leaf extract can be administered orally to patients or can be included in mouth wash or tooth paste to treat or prevent periodontal disease.

TABLE 8

| Group | Image of zymogram band density |
|---|---|
| PBS | 146,000 |
| LPS | 464,000 |
| Melissa and Ginkgo treated | 217,000 |

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of inhibiting angiogenesis and an angiogenesis associated disease, comprising administering an angiogenesis inhibiting effective amount of a composition comprising *Melissa* leaf extract to a subject suffering from said angiogenesis associated disease, wherein the *Melissa* leaf extract is administered in an amount of from about 5 mg to about 2000 mg per day.

2. The method according to claim 1, wherein the composition further comprises *Morus alba* extract.

3. The method according to claim 1, wherein the angiogenesis associated disease is selected from the group consisting of cancer metastasis, angioma, angiofibroma, diabetic retinopathy, premature infant's retinopathy, neovascular glaucoma, corneal disease induced by angiogenesis, involutional macula, macular degeneration, pterygium, retinal degeneration, retrolental fibroplasias, granular conjunctivitis, telangiectasis, pyogenic granuloma, and seborrheic dermatitis.

4. The method according to claim 1, where the amount is from about 10 mg to about 1,000 mg per day.

* * * * *